United States Patent
Bradley et al.

(10) Patent No.: US 6,995,348 B2
(45) Date of Patent: Feb. 7, 2006

(54) OPTICAL DETECTION SYSTEM INCLUDING SEMICONDUCTOR ELEMENT

(75) Inventors: Donal Bradley, Beaconsfield (GB); John De Mello, Clapham (GB); Andrew De Malio, Twickenham (GB)

(73) Assignee: Molecular Vision Limited, London (GB)

( * ) Notice: Subject to any disclaimer, the term of this patent is extended or adjusted under 35 U.S.C. 154(b) by 70 days.

(21) Appl. No.: 10/432,296

(22) PCT Filed: Oct. 10, 2001

(86) PCT No.: PCT/GB01/04521

§ 371 (c)(1),
(2), (4) Date: Nov. 3, 2003

(87) PCT Pub. No.: WO02/42747

PCT Pub. Date: May 30, 2002

(65) Prior Publication Data

US 2004/0065806 A1   Apr. 8, 2004

(30) Foreign Application Priority Data

Nov. 22, 2000 (GB) .................................. 0028482

(51) Int. Cl.
*H01L 31/00* (2006.01)

(52) U.S. Cl. .............. 250/214.1; 250/214 R; 250/573; 257/40; 257/414

(58) Field of Classification Search ............ 250/214.1, 250/573, 575; 257/40, 414; 356/436–442
See application file for complete search history.

(56) References Cited

U.S. PATENT DOCUMENTS

| | | | | |
|---|---|---|---|---|
| 5,107,133 A | * | 4/1992 | Klainer | 250/573 |
| 6,509,574 B2 | * | 1/2003 | Yuan et al. | 250/551 |

FOREIGN PATENT DOCUMENTS

| | | |
|---|---|---|
| WO | WO 00 05166 | 2/2000 |
| WO | WO 01 38857 | 5/2001 |

OTHER PUBLICATIONS

Friend, R.H., et al, Electroluminescense in conjugated polymers, Nature, Jan. 14, 1999, MacMillan Magazine, UK, vol. 397, No. 6715, pp. 121.-128.

Jakeway, S.C. et al, Miniaturized total analysis systems for biological analysis, Fres J. Anal. Chem. 366, 525 (2000).

Manz, A. et al, Miniaturized Total Chemical Analysis Systems: a Novel Concept for Chemical Sensing, Sens Actuators, B1, 244 (1990).

(Continued)

*Primary Examiner*—David Porta
*Assistant Examiner*—Patrick J. Lee
(74) *Attorney, Agent, or Firm*—Warner Norcross & Judd LLP

(57) ABSTRACT

A microfabricated detection system, comprising: a substrate chip; a chamber defined by the substrate chip to which a fluid sample is in use delivered; and at least one detector comprising at least one light-emitting diode including an organic semi-conductor element for emitting light into the chamber and at least one photocell including an organic semiconductor element for receiving light from the chamber.

25 Claims, 1 Drawing Sheet

OTHER PUBLICATIONS

Figure 1:
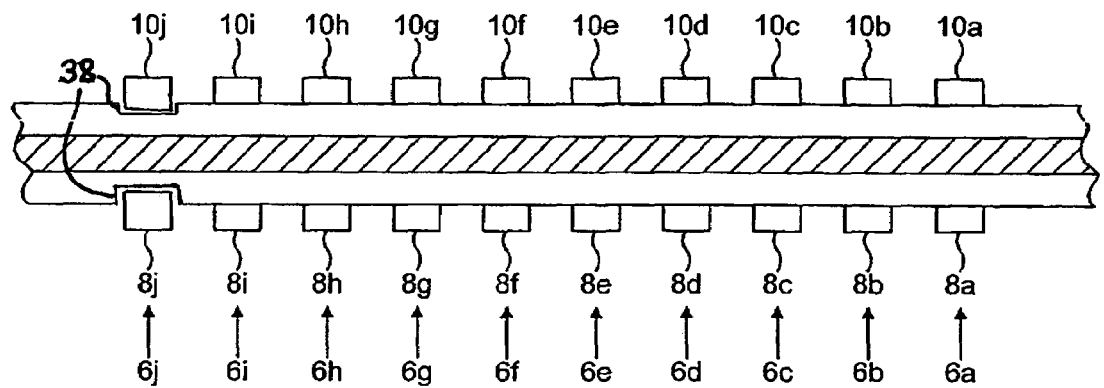

Manz, A. et al, Planar chips technology for miniaturization and integration of separation techniques into monitoring systems, J. Chromatogr., 593,253 (1992).

Woolley,A.T. et al, Functional Integration of PCR Amplification and Capillary Electrophoresis in a Microfabricated DNZ Analysis Device, Anal.Chem., 68, 4081 (1996).

Liang, Z. et al, Microfabrication of a Planar Absorbance and Fluorescence Cell for Integrated Capillary Electrophoresis Devices, Anal. Chem., 68, 1040 (1996).

Manz, A. et al, J. High Resolut. Chormatogr., 16, 433 (1993).

Aora, A. et al, Sub-microliter Electrochemiluminescence Detector—A Model for Small Volume Analysis Systems, Anal Commun, 34, 393 (1997).

Sirichai, S. et al, A capillary electrophoresis microchip for the analysis of photographic developer solutions using indirect fluorescence detection, Analyst, 125, 133 (2000).

Burggraf, N. et al, Holographic refractive index detector for application in microchip-based separation systems, Analyst, 123, 1443 (1998).

Xue, Q. et al, Multichannel Microchip Electrospray Mass Spectrometry, Anal. Chem., 69, 426 (1997).

Shirakawa, H. et al, Chem. Commun., 578 (1977).

Burroughes, J.H. et al, Light-emitting diodes based on conjugated polymers, Nature, 347, pp 539-541 (1990).

Burns, S., Ph.D. Thesis, Cambridge, 1997.

Crabtree, H.J. et al, Shah Convolution Fourier Transform Detection, Anal. Chem., 71, 2130 (1999).

Mallat, S., A Wavelet Tour of Signal Processing, Academic Press Inc., (1999).

Judd, D.B. et al, Color in Business, Science and Industry (3rd edition), John Wiley, 296 (1975).

Lidzey, D.G. et al, Electroluminescence in polymer films, Nature, 386, 135 (1997).

* cited by examiner

OPTICAL DETECTION SYSTEM INCLUDING SEMICONDUCTOR ELEMENT

The present invention relates to an optical detection system.

The accurate determination of chemical and biological parameters has always been of central importance in science. Recently, however, a real need for rapid, on-line measurements at low concentrations has developed within such fields as chemical production, DNA analysis, drug discovery, pharmaceutical screening, medical diagnostics and environmental analysis [1].

In such fields, the analytes, whether small organic molecules or much larger biopolymers, are usually present as minor components. As a result, the discrimination of analytes from other components, which tend to interfere with the analyte detection, is usually the critical step in any analysis.

Chemical sensors have been developed which enable a direct analysis, transducing molecular information of a particular analyte into electronic information. Such sensors provide information in real time and at the exclusion of all other components. The analysis can be refined by incorporating a separation step prior to transduction, which separation lessens the selectivity requirements in detection and improves sensitivity.

Total (chemical) analysis systems (TASs) have been developed which provide all of the stages of a complete analysis in an integrated and automated manner. These stages include sampling, pre-treatment, chemical reactions, analytical separations, analyte detection, product isolation and data analysis. Such TASs have enabled enhancements in on-line analysis, but have a number of significant drawbacks. These include slow sample transport, high reagent consumption, and the need to fabricate interfaces between each of the system components.

More recently, miniaturised total (chemical) analysis systems ($\mu$-TASs) have been developed [2] which exhibit improved analytical performance by virtue of the reduced size. Typically, a $\mu$-TAS is a microfabricated device which is fabricated using conventional micromachining technologies, for example, photolithography, etching, thin-film deposition and bonding, where channels, reactors, filters, injectors and detectors are created on planar glass, silicon or polymeric substrates. Enhancements in performance have been shown experimentally and theoretically [3]. Notably, miniaturisation of flow manifolds leads to reduced reagent consumption, greater separation efficiencies and reduced analysis times.

In $\mu$-TASs, for example, in capillary electrophoresis (CE) chips, injection volumes typically range between $10^{-14}$ and $10^{-10}$ dm$^3$. At a diagnostically relevant target concentration of 1 nanomolar, these volumes include only from about 10 to $10^4$ detectable molecules. High-sensitivity detection is thus a pre-requisite for performing microanalysis.

To date, small volume detection in analytical systems has generally involved optical measurements. This is primarily because most planar chip devices are fabricated from glassy materials which are transparent in the visible region of the electromagnetic spectrum. The two most common techniques for optical detection are absorption and fluorescence.

Absorption techniques present a number of problems as the small volumes employed are not readily reconciled with the requirement for sufficiently long optical pathlengths. Solutions to the pathlength problem have been proposed [5–6]. However, any sensitivity gains are normally at the expense of component resolution, particularly when applied to detection in electrophoretic or chromatographic devices.

Fluorescence techniques have generally proved superior to absorption techniques. For example, laser-induced fluorescence measurements are capable of routinely detecting as few as $10^5$ molecules, and recent developments in ultra-high sensitivity fluorescence detection have allowed single molecule detection on planar chip systems. However, whilst fluorescence techniques are inherently sensitive, these techniques suffer from a number of limitations in terms of cost, portability and applicability.

Alternative techniques have been developed which allow for the detection of non-fluorescent molecules. These techniques include electrochemiluminescence [7], indirect fluorescence [8], and electrochemical and refractive index variation techniques [1, 9]. In addition, capillary electrophoresis microchips have been successfully coupled with electrospray mass spectrometry (MS) [10].

Although these techniques separately provide for improvements in miniaturisation, cost and applicability, no single technique provides a miniaturised, high sensitivity detection system at low cost. A detection system possessing these characteristics, although not essential for laboratory-based analysis, is a pre-requisite for developing portable $\mu$-TASs capable of high-sensitivity measurements in point-of-care and in-the-field applications. Typical applications include environmental monitoring, clinical and medical diagnostics, industrial process control and forensic analysis.

It is thus an aim of the present invention to provide a microfabricated detection system which is of high sensitivity and has low detection limits. It is also an aim of the present invention to provide a detection system which is of low cost.

Accordingly, the present invention provides a microfabricated detection system, comprising: a substrate chip; a chamber defined by the substrate chip to which a fluid sample is in use delivered; and at least one detector comprising at least one light-emitting diode including an organic semiconductor element for emitting light into the chamber and at least one photocell including an organic semiconductor element for receiving light from the chamber.

Preferably, the chamber has a depth of from about 10 to about 500 $\mu$m.

More preferably, the chamber has a depth of from about 50 to about 100 $\mu$m.

Preferably, the chamber has a width of from about 10 to about 100 $\mu$m.

More preferably, the chamber has a width of from about 10 to about 50 $\mu$m.

Preferably, the chamber has a depth-to-width aspect ratio of greater than 1.

More preferably, the chamber has a depth-to-width aspect ratio of at least about 10.

Preferably, the at least one photocell of at least one of the at least one detector faces into the depth of the chamber.

More preferably, the at least one photocell of each detector faces into the depth of the chamber.

Preferably, the at least one light-emitting diode and the at least one photocell of at least one of the at least one detector are in opposed relation.

More preferably, the at least one light-emitting diode and the at least one photocell of each detector are in opposed relation.

Preferably, the at least one light-emitting diode of at least one of the at least one detector is included in a microcavity.

More preferably, the at least one light-emitting diode of each detector is included in a microcavity.

Preferably, the at least one photocell of at least one of the at least one detector is configured to be wavelength selective.

More preferably, the at least one photocell of each detector is configured to be wavelength selective.

Preferably, the at least one photocell of at least one of the at least one detector includes a filter upstream of the organic semiconductor element thereof.

More preferably, the at least one photocell of each detector includes a filter upstream of the organic semiconductor element thereof.

In one embodiment the or each filter is a notch filter.

Preferably, at least one of the least one detector includes a plurality of photocells, with the organic semiconductor elements of the photocells having different absorption spectra and providing a differential response in colour space.

More preferably, each detector includes a plurality of photocells.

In one embodiment the or each detector includes three photocells.

Preferably, the at least one light-emitting diode of at least one of the at least one detector is a multi-layered structure deposited on a surface of the substrate chip.

More preferably, the at least one light-emitting diode of each detector is a multi-layered structure deposited on a surface of the substrate chip.

Preferably, the at least one photocell of at least one of the at least one detector is a multi-layered structure deposited on a surface of the substrate chip.

More preferably, the at least one photocell of each detector is a multi-layered structure deposited on a surface of the substrate chip.

Preferably, the detection system comprises a plurality of spaced detectors.

Preferably, the spacing of the detectors is less than about 500 $\mu$m.

More preferably, the detectors are uniformly spaced.

Preferably, the chamber is a flow channel.

In one embodiment the detectors are spaced along the flow channel.

Preferably, the detection system comprises a drive unit for driving the or each light-emitting diode to emit light.

More preferably, the drive unit is configured to drive the or each light-emitting diode in a pulsed mode to emit light of a high instantaneous brightness.

Yet more preferably, the drive unit is configured to drive the or each light-emitting diode to emit light having an instantaneous brightness of at least about $10^7$ cd/m$^{-2}$.

Preferably, the detection system further comprises a detection unit for receiving signals from the or each photocell.

In preferred embodiments the juxtaposition of the light-emitting diodes and the light-receiving photocells to the substrate chip ensures that emission/collection losses are minimized. Simple calculations as set out in the attached Appendix indicate that analyte concentrations of down to at least $10^{-8}$ mol dm$^{-3}$ should be readily detectable, with lower detection limits being attainable with the use of low-noise techniques, such as phase-sensitive detection.

The detection system also advantageously enables detection simultaneously and independently at a large number of closely-spaced locations along a flow path. Such multi-point detection at points spaced at typically less than 500 $\mu$m provides the spatial resolution for particularly useful analysis. Such resolution is not possible using conventional detectors, such as photomultiplier tubes (PMTs), as the sheer physical size of those detectors renders those detectors unsuitable for on-plane detection.

Furthermore, the detection system advantageously requires only minuscule amounts of sample, is rapid in action, non-invasive, selective and highly efficient, and has a low unit cost. The present invention finds particular application in the general clinical/biological fields by virtue of the ability to perform standard analyses in a superior fashion to conventional instrumentation, offering dramatically reduced analysis times and allowing rapid point-of-care diagnosis.

Figure 2:
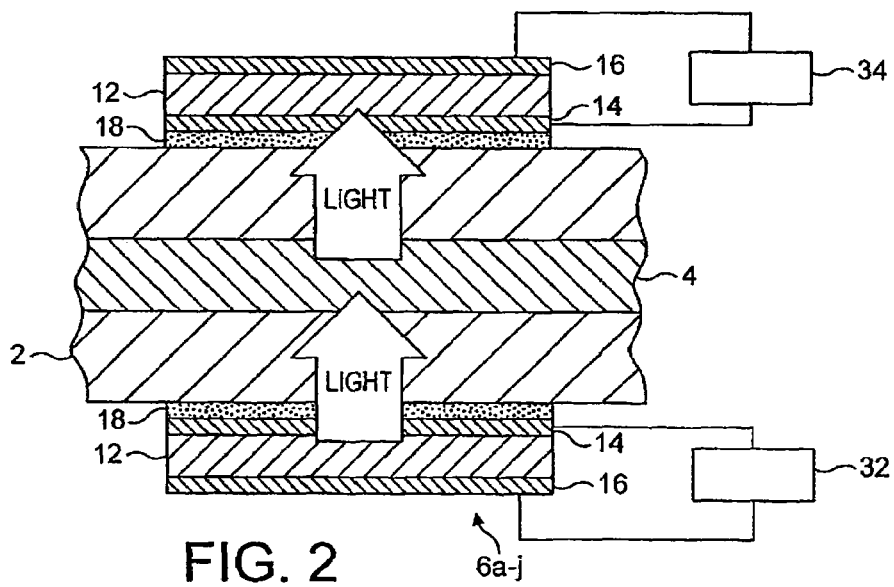

A preferred embodiment of the present invention will now be described hereinbelow by way of example only with reference to the accompanying drawings, in which:

FIG. 1 schematically illustrates a microfabricated detection system in accordance with a preferred embodiment of the present invention; and FIG. 2 illustrates one of the detectors of the detection system of FIG. 1.

The detection system comprises a substrate chip 2, in this embodiment a planar chip, which includes a channel 4 through which a fluid, as a liquid or a gas, for analysis is directed, and a plurality of detectors 6a–j disposed to the substrate chip 2 in spaced relation along the length of the channel 4. In this embodiment the spacing of the detectors 6a–j is less than about 500 $\mu$m. This detection system is referred to as a polymeric detection system.

The detectors 6a–j, in this embodiment each configured to be selective to a particular wavelength, comprise a light-emitting diode 8a–j (LED) and a light-receiving photocell 10a–j disposed in opposed relation to the opposed surfaces of the substrate chip 2.

In this embodiment the substrate chip 2 is formed of one or both of a glass or plastics material, such as polydimethylsiloxane (PDMS), with the channel 4 being typically formed by reactive ion etching. In preferred embodiments the channel 4 has a depth of from about 10 to about 500 $\mu$m, preferably from about 50 to about 100 $\mu$m, and a width of from about 10 to about 100 $\mu$m, preferably from about 10 to about 50 $\mu$m. For low concentration analytes, and a given flow rate, increased sensitivity of detection can be provided by providing the channel 4 with a high depth-to-width aspect ratio. In preferred embodiments the channel 4 has a depth-to-width aspect ratio of at least about 10.

As illustrated in FIG. 2, the light-emitting diodes 8a–j and the photocells 10a–j of the detectors 6a–j are multi-layered structures, in this embodiment semiconducting polymer (SP) structures fabricated in a known manner by the sequential deposition of polymer and electrode materials [11]. The light-emitting diodes 8a–j and the photocells 10a–j each comprise at least one organic semiconductor layer 12, in this embodiment a semiconducting polymer layer, sandwiched between a substantially transparent anode layer 14, in this embodiment of indium tin-oxide (ITO), and a cathode layer 16, in this embodiment a metal. In preferred embodiments the one or more semiconductor layers 12 can be blends of semiconducting polymers.

In preferred embodiments the semiconducting polymers are soluble polymers and the semiconductor layers 12 are fabricated by a printing technique, preferably ink-jet printing. In this way, the light-emitting diodes 8a–j and the photocells 10a–j of the detectors 6a–j can be located precisely along the channel 4. Furthermore, complex patterns are achievable using ink-jet printing techniques, thereby allowing the deposition of intricate arrays of the detectors 6a–j at sub-millimetre scale with high precision. This technique is ideally suited to the low-cost demands of disposable applications. Also, owing to the layer-by-layer fabrication of the light-emitting diodes 8a–j and the photocells 10a–j, the detection system can be integrated with existing microfabricated systems.

The operation of each of the light-emitting diodes 8a–j is such that, when a sufficiently high potential difference is applied thereacross, electrons and holes are injected from the respective ones of the anode and cathode layers 14, 16 and re-combine in the semiconductor layer 12 to form excitons, which excitons subsequently relax to the ground state with the emission of photons. The operation of each of the photocells 10a–j is essentially the converse of that of the light-emitting diodes 8a–j, where the absorption of photons by the semiconductor layer 12 creates excitons which subsequently dissociate to form unbound electrons and holes; with the separated charges drifting under the influence of the internal electric field towards the respective ones of the anode and cathode layers 14, 16 and to an external circuit.

In one configuration for fluorescent analysis, when a fluorescent analyte, such as a chromophore, passes through the channel 4, the fluorescent analyte absorbs photons emitted by the respective light-emitting diodes 8a–j and subsequently re-emits fluorescence photons, which fluorescence photons are detected by the respective photocells 10a–j.

In another configuration for phosphorescent analysis, when a phosphorescent analyte passes through the channel 4, the phosphorescent analyte absorbs photons emitted by the respective light-emitting diodes 8a–j and subsequently re-emits phosphorescence photons, which phosphorescence photons are detected by the respective photocells 10a–j.

In a further configuration for absorption analysis, where a sufficiently large optical path length is provided between the light-emitting diodes 8a–j and the photocells 10a–j of each of the detectors 6a–j, when an absorptive analyte passes through the channel 4, the absorptive analyte absorps photons emitted by the respective light-emitting diodes 8a–j, which absorption is detected as a reduction in the transmission of photons from the respective light-emitting diodes 8a–j as detected by the respective photocells 10a–j.

In one mode of analysis, the analyte concentrations are measured at each of the detectors 6a–j simultaneously.

In another mode of analysis, a Shah Convolution Fourier Transform (SCOFT) detection is utilised [15]. In SCOFT, the emission intensities from moving analyte plugs are measured by the detectors 6a–j at uniformly spaced locations along the channel 4. Since, in most separation techniques, for example, capillary electrophoresis and high-pressure liquid chromatography (HPLC), analyte plugs move at constant speed, the emission intensities at each detector 6a–j can be summed electronically to yield a time-dependent signal of fixed frequency. The frequency of the signal is determined uniquely by the mobility of the analyte and thus may be used as a means of analyte identification. For multi-component systems, additional components will be present in the frequency domain, again at locations determined uniquely by the mobilities.

In a further mode of analysis, the emission intensity is measured at each of the detectors 6a–j independently, and wavelet analysis, which ensures near-optimal localisation in real and reciprocal space [16], is employed to process the data. In this way, and unlike SCOFT detection, spatial information is preserved, increasing the information content and allowing the determination of variations in, for example, electrophoretic mobility with distance.

Finally, it will be understood that the present invention has been described in its preferred embodiment and can be modified in many different ways without departing from the scope of the invention as defined by the appended claims.

In one modification, the light-emitting diodes 8a–j can each be included in an optional microcavity 38 to provide excitation sources having improved spectral properties. Organic semiconductors, in particular semiconducting polymers, typically have broad emission properties, while, for the purposes of optical detection, a narrow excitation source is desirable. By including each of the light-emitting diodes 8a–j in a microcavity 38 of appropriate optical pathlength, the excitation light from each of the light-emitting diodes 8a–j has enhanced mono-chromaticity. Such cavities may be fabricated by the alternate thermal deposition of materials with sharply differing refractive indices to form simple low-cost Bragg reflectors [14].

In another modification, where appropriate, notch filters 18 can be provided directly in front of each of the photocells 10a–j selectively to filter out photons transmitted directly from the light-emitting diodes 8a–j, which excitation photons would otherwise mask the less-intense fluorescence or phosphorescence photons. The thickness and location of the filters 18 shown in FIG. 2 are exemplary onlym and can be modified to any desired thickness or location. Also, it is noted that the filters ate entirely optional.

In a further modification, phase-sensitive lock-in techniques can be employed to discriminate between excitation photons transmitted directly from the light-emitting diodes 8a–j and the less-intense emission photons from a phosphorescent analyte. With this configuration, the use of filters 18 for example, notch filters, is optional.

In a yet further modification, each of the detectors 6a–j includes a plurality, in this embodiment three, of adjacent photocells 10a–j having semiconductor layers 12 formed of materials with well-separated absorption spectra. The differential response of the plurality of photocells 10a–j allows a 'colour', or, more accurately, a two-dimensional co-ordinate in colour space (as defined by the Commission Internationale del 'Éclairage [17]), to be assigned to the emitting analyte, providing a simple and effective means of identification. This planar detection arrangement can be contrasted with conventional optical spectrometers, where a diffraction/reflection grating or prism is normally used to disperse the light which would then be scanned over a fixed point-detector or imaged onto an array of detectors to extract spectral information.

In a still further modification, the light-emitting diodes 8a–j with appropriate heat sinking are operated under relatively low duty-cycle pulsed operation, which pulsed operation allows the development of high instantaneous brightnesses, typically brightnesses of the order of $10^7$ cd/m$^2$ [18]. The high instantaneous changes in the photoluminescence, together with the use of low-noise phase-sensitive detection techniques, for example, lock-in amplification, enable optical detection at particularly low concentrations. In a preferred embodiment the light-emitting diodes 8a–j are driven by a square-wave voltage source, also referred to as a drive unit 32. In this regard, it is expected that the enclosure of the light-emitting diodes 8a–j in microcavities, together with the use of pulsed driving voltages, will provide for the fabrication of microarrays of closely-spaced laser diodes. The drive unit 32 is entirely optional and depends on the desired use.

In another embodiment, the detection system can include a detection unit 34 for receiving signals from one or more photocells.

REFERENCES

1. S. C. Jakeway, A. J. de Mello, E. L. Russell, Fres. *J. Anal. Chem.*, 366, 525 (2000).
2. A. Manz, N. Graber, H. M. Widmer, *Sens Actuators*, B1, 244 (1990).
3. A. Manz, D. J. Harrison, E. M. J. Verpoorte, J. C. Fettinger, A. Paulus, H. Ludi, H. M. Widmer, *J. Chromatogr.*, 593,253 (1992).
4. A. T. Woolley, D. Hadley, P. Landre, A. J. deMello, R. A. Mathies, M. A. Northrup, *Anal. Chem.*, 68, 4081 (1996).
5. Z. Liang et al, *Anal. Chem.*, 68, 1040 (1996).
6. A. Manz et al, *J. High Resolut. Chromatogr.*, 16, 433 (1993).
7. A. Arora, A. J. deMello, A. Manz, *Anal. Commun.*, 34, 393 (1997).
8. S. Sirichai, A. J. de Mello, *Analyst*, 125, 133 (2000).
9. N. Burggraf, B. Krattiger, A. J. de Mello, N. F. de Rooij, A. Manz, *Analyst*, 123, 1443 (1998).
10. Q. Xue, F. Foret, Y. M. Dunayevskiy, P. M. Zavracky, N. E. McGruer, B. L. Karger, *Anal. Chem.*, 69, 426 (1997).
11. R. H. Friend et al, *Nature*, 397, 121 (1999).
12. H. Shirakawa, E. J. Lewis, A. G. Lewis, A. G. MacDiarmid, C. K. Chiang, A. J. Heeger, *Chem. Commun.*, 578 (1977).
13. J. H. Burroughes, D. D. C. Bradley, A. R. Brown, R. N. Marks, K. MacKay, R. H. Friend, P. L. Burn, A. B. Holmes, *Nature*, 341, 531 (1990).
14. S. Burns, *Ph.D. Thesis*, Cambridge, 1997.
15. H. J. Crabtree, M. U. Kopp, A. Manz, *Anal. Chem.*, 71, 2130 (1999).
16. S. Mallat, 'A Wavelet Tour of Signal Processing', Academic Press Inc, (1999).
17. D. B. Judd, G. Wyszecki, 'Color in Business', *Science and Industry* (3rd edition), John Wiley, 296 (1975).
18. D. G. Lidzey, D. D. C. Bradley, S. Alvarado, P. F. Seidler, *Nature*, 386, 135 (1997).

Appendix: Estimating the Sensitivity of Polymer Detection Systems

An estimate of the system sensitivity may be obtained from:

$$j_{DET} = \alpha d \sigma Q_{DET} Q_{PL} Q_{EL} N_T j_{LED}$$

where: $j_{DET}$ is the current density of the photocell 10a–j α is the collection efficiency of the photocell 10a–j d is the spacing of the light-emitting diode 8a–j and the photocell 10a–j σ is the absorption cross section of the chromophore under study $Q_{DET}$, $Q_{PL}$, and $Q_{EL}$ are the quantum efficiencies of the photocell 10a–j, the chromophore in solution and the light-emitting diode 8a–j $N_T$ is the density of the chromophore $j_{LED}$ is the current density in the light-emitting diode 8a–j Typical parameters for the detection system are α=0.1, d=$10^{-5}$ m$^2$, σ=$10^{-18}$ M$^2$, $Q_{DET}$=0.1, $Q_{PL}$=0.1, $Q_{EL}$=0.01 and $j_{LED}$=$10^3$ am$^{-2}$, which yields $j_{DET}$=$10^{-25}$ $N_T$.

Therefore, since the dark current in polymer photocells is typically $10^{-6}$ Am$^{-2}$ or less, chromophore densities in excess of about $10^{19}$ m$^{-3}$ (≈$10^{-8}$ mol dm$^{-3}$) should in principle be detected using the detection system with a simple two-point dc measurement using an electrometer.

In fact, the above calculation is rather pessimistic. State-of-the-art LEDs have quantum efficiencies of about 0.1, and photocell efficiencies in excess of unity are common under an applied reverse bias. A relatively poor collection efficiency has also been assumed for the photocell 10a–j. Further, a low current density through the light-emitting diode 8a–j has been assumed. In practice, steady-state current densities in existing LEDs ate typically ten times higher. Moreover, the light-emitting diode 8a–j when used in pulsed operation can give instantaneous brightnesses of at least $10^7$ cdm$^{-2}$.

What is claimed is:

1. A microfabricated detection system, comprising:
   a substrate chip;
   a chamber defined by the substrate chip to which a fluid sample is delivered; and
   at least one detector comprising at least one light-emitting diode including an organic semiconductor element for emitting light into the chamber and at least one photocell including an organic semiconductor element for receiving light from the chamber.
2. The detection system of claim 1, wherein the chamber has a depth of from about 10 to about 500 μm.
3. The detection system of claim 2, wherein the chamber has a depth of from about 50 to about 100 μm.
4. The detection system of claim 1, wherein the chamber has a width of from about 10 to about 100 μm.
5. The detection system of claim 4, wherein the chamber has a width of from about 10 to about 50 μm.
6. The detection system of claim 1, wherein the chamber has a depth-to-width aspect ratio of greater than 1.
7. The detection system of claim 6, wherein the chamber has a depth-to-width aspect ratio of at least about 10.
8. The detection system of claim 7, wherein the at least one photocell of at least one of the at least one detector faces into the depth of the chamber.
9. The detection system of claim 8, wherein the at least one light-emitting diode and the at least one photocell of at least one of the at least one detector are in opposed relation.
10. The detection system of claim 1, wherein the at least one light-emitting diode of at least one of the at least one detector is included in a microcavity.
11. The detection system of claim 1, wherein the at least one photocell of at least one of the at least one detector is configured to be wavelength selective.
12. The detection system of claim 1, wherein the at least one photocell of at least one of the at least one detector including a filter upstream of the organic semiconductor element thereof.
13. The detection system of claim 12, wherein the filter is a notch filter.
14. The detection system of claim 1, wherein at least one of the least one detector includes a plurality of photocells, with the organic semiconductor elements of the photocells having different absorption spectra and providing a differential response in colour space.
15. The detection system of claim 1, wherein the at least one light-emitting diode of at least one of the at least one detector is a multi-layered structure deposited on a surface of the substrate chip.
16. The detection system of claim 1, wherein the at least one photocell of at least one of the at least one detector is a multi-layered structure deposited on a surface of the substrate chip.
17. The detection system of claim 1, comprising a plurality of spaced detectors.
18. The detection system of claim 17, wherein the spacing of the detectors is less than about 500 μm.
19. The detection system of claim 1, comprising a plurality of detectors, wherein the detectors are uniformly spaced.

20. The detection system of claim 1, wherein the chamber is a flow channel.

21. The detection system of claim 20, wherein the detectors are spaced along the flow channel.

22. The detection system of claim 1, comprising a drive unit for driving the at least one light-emitting diode to emit light in a pulsed mode to emit light of a high instantaneous brightness.

23. The detection system of claim 22, wherein the drive unit is configured to drive the at least one light-emitting diode to emit light having an instantaneous brightness of at least about $10^7$ cdm$^{-2}$.

24. The detection system of claim 1, further comprising a detection unit for receiving signals from the at least one photocell.

25. The detection system of claim 1 wherein the chamber receives and the detector detects substantially only the fluid sample.

* * * * *